(12) United States Patent
Presura et al.

(10) Patent No.: US 8,417,307 B2
(45) Date of Patent: Apr. 9, 2013

(54) BLOOD OXIMETER

(75) Inventors: Cristian Presura, Veldhoven (NL); Carsten Heinks, Neuenhaus (DE); Olaf Such, Aachen (DE); Gary Nelson Garcia Molina, Eindhoven (NL); Gert Hooft, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 12/679,966

(22) PCT Filed: Sep. 24, 2008

(86) PCT No.: PCT/IB2008/053874
§ 371 (c)(1),
(2), (4) Date: May 11, 2010

(87) PCT Pub. No.: WO2009/040740
PCT Pub. Date: Apr. 2, 2009

(65) Prior Publication Data
US 2010/0240973 A1    Sep. 23, 2010

(30) Foreign Application Priority Data

Sep. 27, 2007 (EP) .................................. 07117427

(51) Int. Cl.
*A61B 5/1455* (2006.01)
*A61B 5/02* (2006.01)
(52) U.S. Cl. .................. 600/324; 600/335; 600/485
(58) Field of Classification Search ........... 600/309–344
See application file for complete search history.

(56) References Cited

U.S. PATENT DOCUMENTS

| 5,595,176 A | 1/1997 | Yamaura |
| 5,596,986 A | 1/1997 | Goldfarb |

(Continued)

FOREIGN PATENT DOCUMENTS

| RU | 2173082 C | 9/2001 |
| RU | 2221485 C | 1/2004 |

(Continued)

OTHER PUBLICATIONS

Dougherty et al: "A Prototype Instrument Combining Laser Doppler Flowmetry and Reflection Pulse Oximetry"; Clinical Physics and Physiological Measurement; 1992, vol. 13, No. 2, pp. 105-114.

(Continued)

*Primary Examiner* — Eric Winakur
*Assistant Examiner* — Marjan Fardanesh

(57) ABSTRACT

The invention relates to a blood oximeter for measuring the oxygenation and at least one other parameter of flowing blood in living tissue. According to the invention, the blood oximeter comprises two lightsources (2, 3) emitting light of different wavelengths into tissue, and preferably a light detector (4) for detecting a transmitted and/or reflected part of the light emitted into the tissue, wherein at least one of the light sources is a laser with a laser cavity emitting a laser beam, the laser being adapted to allow a part of the laser beam which is scattered by the tissue to re-enter into the laser cavity, and wherein a laser beam sensor (7, 8) for measuring the light emitted from the laser is provided, the laser beam sensor (7, 8), thus, obtaining a signal which varies in accordance with the self-mixing interferometric effect between the original laser beam and the scattered laser beam. Accordingly, such a blood oximeter is provided that performs well at low perfusion and which further allows for reliable measurements.

16 Claims, 7 Drawing Sheets

U.S. PATENT DOCUMENTS

| | | |
|---|---|---|
| 6,859,658 B1 * | 2/2005 | Krug .............................. 600/323 |
| 2004/0034294 A1 | 2/2004 | Kimball et al. |
| 2005/0059868 A1 | 3/2005 | Schurman |
| 2006/0287588 A1 | 12/2006 | Yarita |
| 2007/0049811 A1 | 3/2007 | Kobayashi et al. |

FOREIGN PATENT DOCUMENTS

| | | |
|---|---|---|
| WO | 9639927 A1 | 12/1996 |
| WO | 9815224 A1 | 4/1998 |
| WO | 0028887 A1 | 5/2000 |
| WO | 2006085278 A2 | 8/2006 |
| WO | 2006126152 A2 | 11/2006 |

OTHER PUBLICATIONS

Petrig et al: "Ray Tracing Model for the Estimation of Power Spectral Properties in Laser Doppler Velocimetry of Retinal Vessels and Its Potential Application to Retinal Vessel Oximetry"; Optics Express, Dec. 2005, vol. 13, No. 26, 10 Page Document.

Lopez-Silva et al: "Transmittance Photoplethysmography and Pulse Oximetry With Near Infrared Laser Diodes"; Proceedings of the 21st IEEE Instrumental and Measurement Technology Conference, May 2004, pp. 718-722.

* cited by examiner

BLOOD OXIMETER

FIELD OF THE INVENTION

The invention relates to the field of blood oximeters and the measurement of oxygenation of blood flowing in living tissue.

BACKGROUND OF THE INVENTION

Blood oximeters, especially pulse oximeters are widely used for measuring oxygenation of blood of a patient since they provide a simple non-invasive method for monitoring the percentage of hemoglobin which is saturated with oxygen. Continuous monitoring of oxygen saturation via pulse oximetry is a standard of care for use in operating rooms, post anesthesia care units, critical care units, emergency departments etc.

A pulse oximeter typically comprises two small light-emitting diodes that emit light of different wavelengths, typically in the red and the infrared part of the spectrum, respectively. The part of the emitted light transmitted through or reflected by tissue of a part of the patient's body, typically a fingertip or an ear lobe, is collected with a photodiode. Since absorption of these different wavelengths differs between oxyhemoglobin and its deoxygenated form, from the ratio of the collected red and infrared light, respectively, the percentage of hemoglobin which is saturated with oxygen can be determined. Such a pulse oximeter is known from U.S. Pat. No. 5,595,176.

It is an essential feature of conventional pulse oximeters that they rely on the pulsed part of the collected signal in order to discriminate the pulsating blood flow from the static tissue. Accordingly, pulse oximetry performs pure at low blood perfusion. Further, involuntary patient movements can be cumbersome for such measurements leading to poor measuring accuracy or defective measurement results.

SUMMARY OF THE INVENTION

It is an object of the invention to provide such a blood oximeter that performs well at low perfusion and which further allows for reliable measurements.

This object is achieved by a blood oximeter for measuring the oxygenation and at least one other parameter of flowing blood in living tissue, comprising two light sources emitting light of different wavelengths into the tissue, wherein at least one of the light sources is a laser with a laser cavity emitting a laser beam, the laser being adapted to allow a part of the laser beam which is scattered by the tissue to re-enter into the laser cavity, and wherein a laser beam sensor for measuring the light emitted from the laser is provided, the laser beam sensor, thus, obtaining a signal which varies in accordance with the self-mixing interferometric effect between the original laser beam and the scattered laser beam.

Accordingly, it is an important feature of the invention that at least one light detector of the blood oximeter is designed as a laser which is adapted for self-mixing interferometry (SMI). This means that light emitted from the laser and scattered by the tissue is allowed to re-enter into the laser cavity. The interference between the light reflected back into the laser cavity and the light already present in the laser cavity causes power fluctuations in the laser. These power fluctuations are measurable with the laser beam sensor since the light that re-enters the laser cavity is reflected back from moving objects like moving blood cells, and, thus, its frequency is Doppler shifted. As a consequence, the power fluctuations in the laser cavity are determined by the Doppler frequency. Accordingly, the velocity of moving blood cells can be measured with the use of the known Doppler formula that connects the frequency shift and the velocity. Thus, the invention provides for the possibility of blood oximetry and laser velocimetry in one single device having multiple advantages as set out in the following.

In general, the laser beam can be directly irradiated onto the tissue without any further optical components. However, according to a preferred embodiment of the invention, a lens is provided for illuminating the laser beam into the tissue through this lens. For this lens, different focal lengths can be used. However, according to a further preferred embodiment of the invention, the focal length of the lens for illuminating the laser beam into the tissue is equal or less than 2 mm. This way, the reflected part of the light is collected and, thus, more light can re-enter into the laser cavity. Accordingly, the signal from the laser beam sensor shows a better S/N-ratio.

Generally, in operation of the blood oximeter, the illuminated tissue can be held at a distance from the laser and/or from the lens. This means that an air gap would be provided between the laser source and the tissue. However, according to a preferred embodiment of the invention, the lens is adapted to directly contact the illuminated tissue. This has the advantage that movements of the tissue relative to the laser can be avoided or at least minimized. Accordingly, Doppler shift effects due to tissue movement can be reduced.

The blood oximeter can be operated continuously. However, according to a preferred embodiment of the invention, a pulse controller is provided that allows for a pulsed operation of the laser. Especially, this pulse controller can be adapted for operating the laser during a measuring time of 20 ms or less at an operation frequency of approximately 1 Hz. This allows for an operation in a low power regime which is advantageous with respect to the kind of power supply used, especially in the case of the blood oximeter as a portable device.

In general, the blood oximeter does not have to comprise any further facilities. However, according to a preferred embodiment of the invention, a force actuator is provided for pressing the laser against the illuminated tissue with a predefined pressure. This provides for the possibility of additionally measuring the blood pressure as set out in more detail further below.

Generally, the pressure of the force actuator can be a predefined constant pressure. However, according to a preferred embodiment of the invention, a pressure controller is provided for applying a predefined pressure which changes in time. This allows for accurate blood pressure measurements.

Further, according to a preferred embodiment of the invention, a light detector for detecting a transmitted and/or reflected part of the light emitted into the tissue is provided. This light detector allows for conventional pulse oximetry.

According to a further preferred embodiment of the invention, a motion detector is provided for detecting a motion of the irradiated tissue on the basis of the signal of the laser beam sensor and the signal of the light detector. Further, according to a preferred embodiment of the invention, a motion processing unit is provided for rejecting a measurement due to detected motions of the tissue or for correcting a measurement based on detected motions of the tissue. This means that according to this preferred embodiment of the invention it is made use of the two different signals received by the light detector and the laser beam sensor, respectively, in order to eliminate or at least detect artifacts which originate from relative movements of the irradiated tissue relative to the laser and not from the blood flow itself. If too much movement of the tissue relative to the laser is detected the measurement is rejected and it can be indicated that the measurement has to be repeated. Further, it is also possible to correct such a measurement which means that reliable results are obtained though the tissue is moved relative to the laser.

As set out above, it might be sufficient if only one of the light sources of the blood oximeter is designed as a laser. However, according to a preferred embodiment of the invention, both light sources are designed as a laser with a corresponding laser beam sensor, respectively. This provides for further possibilities as described in the following.

In general, the blood oximeter is adapted to provide a SpO2 value based on the ratio of the intensities of the light received by the light detector and transmitted and/or reflected from the first light source and the second light source, respectively. However, according to a preferred embodiment of the invention, a SO2 unit is provided for determining and indicating a SO2 value based on the signals of both of the laser beam sensors. This means that according to this preferred embodiment of the invention, there is not only the possibility to measure and indicate the oxygenation of blood under normal circumstances with sufficient perfusion but also at low perfusion when pulsation of the blood flow due to the heart beat is minimal. Further, this preferred embodiment of the invention also allows for a quick start of the oximeter because the SO2 measurement can be done in the first measurement cycle which can be as short as 20 ms or less.

BRIEF DESCRIPTION OF THE DRAWINGS

These and other aspects of the invention will be apparent from and elucidated with reference to the embodiments described hereinafter.

In the drawings.

DETAILED DESCRIPTION OF EMBODIMENTS

Figure 1:
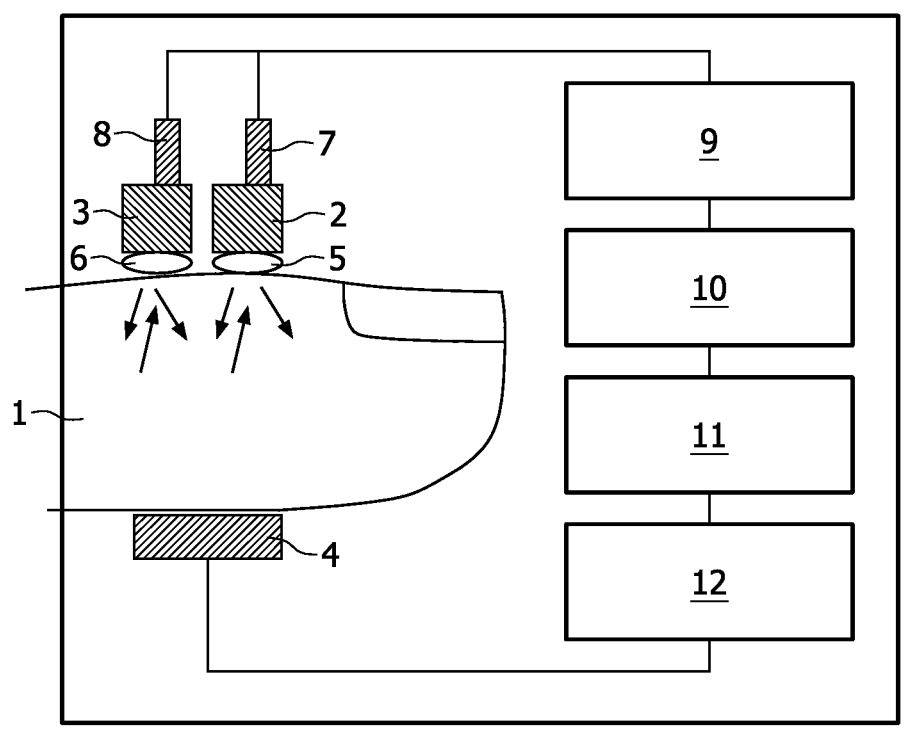
FIG. 1 is a schematic view of a blood oximeter according to a first preferred embodiment of the invention.

From FIG. 1 a schematic view of a blood oximeter according to a first preferred embodiment of the invention can be seen. This blood oximeter is used on a fingertip 1 of a patient and comprises a red laser 2 emitting light in the red part of the light spectrum, an infrared laser 3 emitting light in the infrared part of the light spectrum, and a pulse oximetry photodiode 4. The red laser 2 and the infrared laser 3 are each provided with a lens 5, 6 and with a monitoring photodiode 7, 8, respectively. Both lenses 5, 6 have a focal length of 1.5 mm and are provided between the fingertip 1, and the red laser 2 and the infrared laser 3, respectively. Since the fingertip 1 directly contacts the lenses 5, 6, relative movement of the fingertip 1 with respect to the lasers 2, 3 is minimized. Further, monitoring photodiodes 7, 8 for the red laser 2 and the infrared laser 3, respectively, are provided for measuring the light emitted from each laser 2, 3.

The blood oximeter according to the first preferred embodiment shown in FIG. 1 is operated as follows: Since the red laser 2 operates at a wavelength of 660 mm and the infrared laser 3 operates at a wavelength of 950 mm, the signals received by the pulse oximetry photodiode 4 can be used in a conventional and well known way in order to determine the oxygenation of blood by pulse oximetry. Further, since the red laser 2 and the infrared laser 3 both are adapted to allow a part of the laser beam which is respectively emitted by these lasers 2, 3, to re-enter into the respective laser cavity, self-mixing interferometric effects are achieved in the lasers 2, 3. This means that due to the part of the laser beam that re-enters into the cavity of the respective laser 2, 3, power fluctuations of the lasers 2, 3 occur. These power fluctuations are observed with the help of monitoring photodiodes 7, 8 which measure the light emitted from the respective laser 2, 3.

As already stated above, power fluctuations of the lasers 2, 3 are due to the fact that the part of the laser beam that re-enters a respective laser 2, 3 is Doppler shifted because of the moving red blood cells from which the light is reflected. The Doppler shift is related to the velocity of the red blood cells according to the Doppler formula:

$$\Delta f = \frac{2v}{\lambda} \tag{1}$$

Therein, $\Delta f$ is the Doppler shift, v is the velocity of the red blood cells and $\lambda$ is the irradiated wavelength.

Figure 2A:
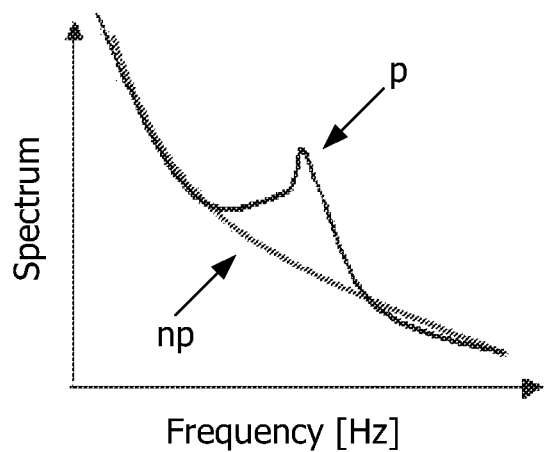
FIG. 2a is a graph of the Doppler shift spectrum for the infrared laser at two moments in time, i.e. during pulsation of the artery and for non-pulsating artery.
Figure 2B:
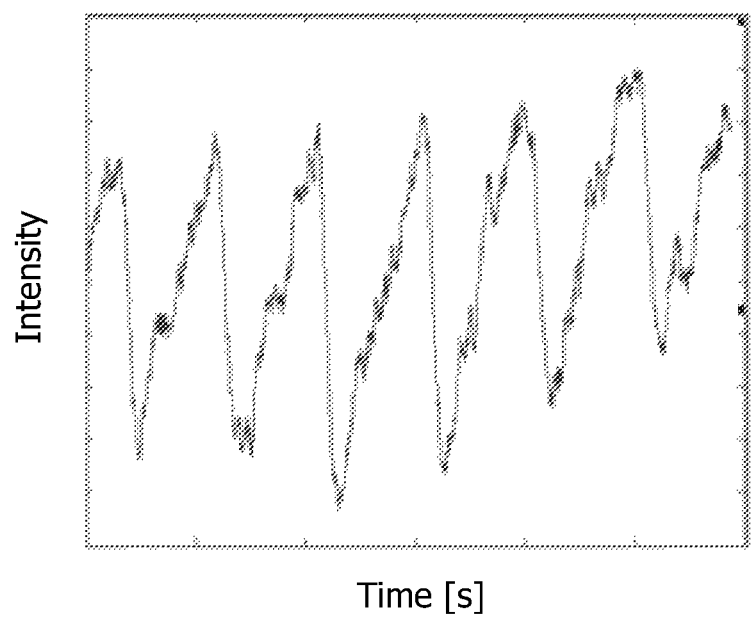
FIG. 2b a graph of the pulsating part of the spectrum with its changes in time.

From FIG. 2a the Doppler shift spectrum for the infrared laser 3 can be seen at two moments in time, i.e. during pulsation of the artery and for non-pulsating artery. This means that the Doppler shift spectrum consists of two parts: A pulsating part (p) and a non-pulsating part (np). The pulsating part is related to the part of the blood moving in the artery. Here, the amount of blood that flows changes with the pulse as well as the distribution of velocities. As it is known, the velocity of blood in veins is constant and does not "feel" the pulse. The veins, thus, reflect in the non-pulsating part of the spectrum. From FIG. 2b, the pulsating part of the spectrum is shown with its changes in time. This reflects the heart beat.

According to the first preferred embodiment described here, this Doppler shift information is combined with a conventional blood oximeter. The amount of laser light scattered by a single red blood cell does not significantly depend on the concentration of oxygen. However, the amount of light absorbed is strongly dependent on the oxygen concentration. This is the principle of conventional pulse oximetry: The more oxygen is in the artery the more infrared light is absorbed and the less red light is absorbed.

The Doppler spectrum can be analyzed in a manner similar to the usual pulse oximetry. For example, the energy of the spectrum in the pulsating area for the red laser 2 can be considered:

$$S_{red}(\omega_1, \omega_2, t) \tag{2}$$

This value changes in time according to the pulse of the patient. Thus, a part of this value represents light scattered by the blood flowing in the artery which can be better investigated taking into account the corresponding frequency range which can then be related to velocities:

$$S_{red}(\omega_1,\omega_2,t) = S_{red}^{const}(\omega_1,\omega_2) + S_{red}^{artery}(\omega_1,\omega_2,t) \quad (3)$$

If only single scattering events are considered it can be assumed to some extend that the component that is reflected by the artery is proportional to the number of red cells which are responsible for scattering, and, thus, proportional to the amount of blood pulsating in the artery B(t):

$$S_{red}^{artery}(\omega_1,\omega_2,t) \approx B(t) f_{red}(\omega_1,\omega_2,c_A,c_V) \quad (4)$$

The second term $f_{red}$ is constant in time and depends on the oxygen concentration in the artery $c_A$ and in veins $c_V$, respectively, as well as other local factors such as the distribution of blood cell velocities. It directly quantifies the amount of light in this frequency range ($\omega_1$, $\omega_2$) that was absorbed.

If the changes in the pulse are measured, this yields:

$$\Delta S_{red}(\omega_1,\omega_2,t) \approx \Delta B(t) f_{red}(\omega_1,\omega_2,c_A,c_V) = \Delta S_{red}^{artery}(\omega_1,\omega_2,t) = \Delta B(t) f_{red}(\omega_1,\omega_2,c_A) \quad (5)$$

As usual in pulse oximetry, only arterial variations can be seen. In addition, this is only related to blood scattered by the artery if simplified to single scattering events.

The same can be written for the infrared laser 3, wherein the amount of blood pulsating B(t) is the same:

$$\Delta S_{ired}(\omega_1,\omega_2,t) \approx \Delta B(t) f_{ired}(\omega_1,\omega_2,c_A) \quad (6)$$

By dividing the two, the term B(t) that gives the amount of pulsating blood can be removed:

$$\frac{\Delta S_{red}(\omega_1,\omega_2,t)}{\Delta S_{ired}(\omega_1,\omega_2,t)} = f(\omega_1,\omega_2,c_A) \quad (7)$$

Further, corrections for the amount of light given by the lasers 2, 3 and which may fluctuate in time can be done:

$$\frac{\Delta S_{red}(\omega_1,\omega_2,t)}{\Delta S_{ired}(\omega_1,\omega_2,t)} \frac{I_{ir}^{DC}}{I_r^{DC}} = f(\omega_1,\omega_2,c_A) \quad (8)$$

If not only single scattering events are considered, a function $f(\omega_1, \omega_2, c_A, c_V)$ has to be used which can be determined by calibration. After calibration, thus, a relation between the oxygen concentration in artery $c_A$ and the oxygen concentration in veins $c_V$ can be measured by comparing the red and the infrared spectra.

In the case of going beyond single scattering events, the two terms, corresponding to the veins and the artery, respectively, have to be disentangled. More degrees of freedom may be used, such as different frequency ranges. The distribution of velocities in veins and artery are different and they will be different in different parts of the Doppler shift spectra. In addition, the terms that do not pulsate can be used. Such terms are more related to blood flowing in the veins which does not pulsate. Using all this information it is possible to determine the oxygen in the artery and in the veins, respectively, more accurately.

Above terms only reflect pulse changes. However, the method can be extended to measurements at low perfusion where practically no pulse is present. In such a case it has to be relied on the whole spectrum which is time independent because there is no pulse:

$$\frac{S_{red}(\omega_1,\omega_2)}{S_{ired}(\omega_1,\omega_2)} \frac{I_{ir}^{DC}}{I_r^{DC}} = f(\omega_1,\omega_2,c_A,c_V) \quad (9)$$

If the whole spectrum is integrated, an average concentration in blood is received. This is, thus, a SO2 value. This method can also be used in cases when the pulsating component of the blood is intentionally removed. In such cases, when there is no change in the blood volume, the Doppler information given by formula (9) can still be used to get the oxygen concentration of blood.

Further, this method can also be used for low power consumption and/or a quick start of the SO2 oximeter. This is possible because the measurement is done in a very short time, i.e. about 10-20 ms, and no complete pulse has to be monitored. In order to work in the low power regime, the lasers 2, 3 are only switched on for 10-20 ms per second in the case of SO2 measurement. Typical consumption of the lasers 2, 3 is about 1 mW in cw-mode. Thus, few tenths of microseconds can be achieved in pulsating mode. This is also why a quick start is possible since it is not necessary to wait for multiple pulses.

As can be seen from FIG. 1, the blood oximeter according to the first preferred embodiment of the invention is provided with a pulse controller 9 for operating the blood oximeter in a pulsed mode, and with a SO2 unit 10 for determining and indicating an SO2 value as described above. Further, the blood oximeter according to the first preferred embodiment comprises a motion detector 11 and a motion processing unit 12 which are operated as set out in the following:

One of the main problems of conventional blood oximeters are motion artifacts during involuntary patient movement. Such artifacts occur when a patient's movements cause the blood oximeter to incorrectly interpret the movements as a pulse signal or when the motion artifact prevents accurate detection of the patient's real pulse signal. This may lead to increasing false alarms and erroneous measurements.

With the blood oximeter according to the first embodiment of the invention, both light sources are designed as lasers 2, 3 adapted for self-mixing interferometry. This provides additional information related to the movement of the blood oximeter with respect to the irradiated tissue, as from a fingertip 1 of the patient. This information can be used to correct the artifacts present in the pulse oximetry photodiode 4 or simply to reject the data as unreliable due to the detected movements.

Figure 3:
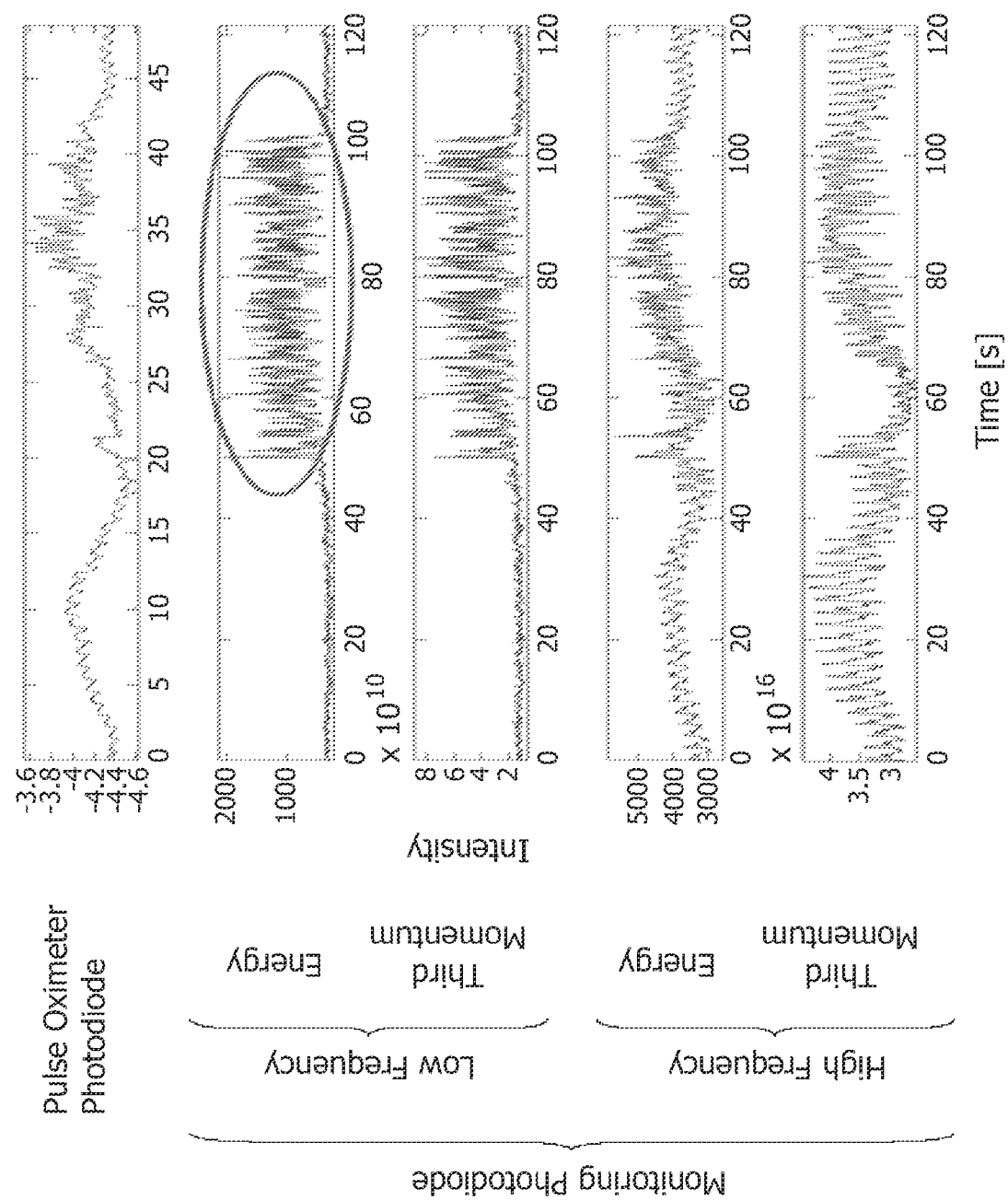
FIG. 3 spectra taken with the pulse oximetry photodiode and taken with the monitoring photodiode of the red laser are shown.

From FIG. 3 spectra taken with the pulse oximetry photodiode 4 and taken with the monitoring photodiode 7 of the red laser 2, respectively, are shown. The signals received with monitoring photodiode 7 are shown for low frequencies and for high frequencies, respectively, and in both cases for energy and third momentum thereof.

As can be seen from the spectrum taken with the pulse oximetry photodiode 4, at time 20 s movements start and, thus, no more heart beat can be observed in the signal of the pulse oximetry photodiode 4. In order to avoid any misinterpretation of this signal from the pulse oximetry photodiode 4, the motion detector 10 is fed with the signal from the monitoring photodiode 7. As can be seen from FIG. 3, especially the spectra from the monitoring photodiode 7 for low frequencies show a prominent signal change at time 20 s (encircled). Accordingly, by monitoring the signal from the monitoring photodiode 7 movements can be detected and, thus, the measurement can be rejected by motion processing unit 12.

Figure 4:
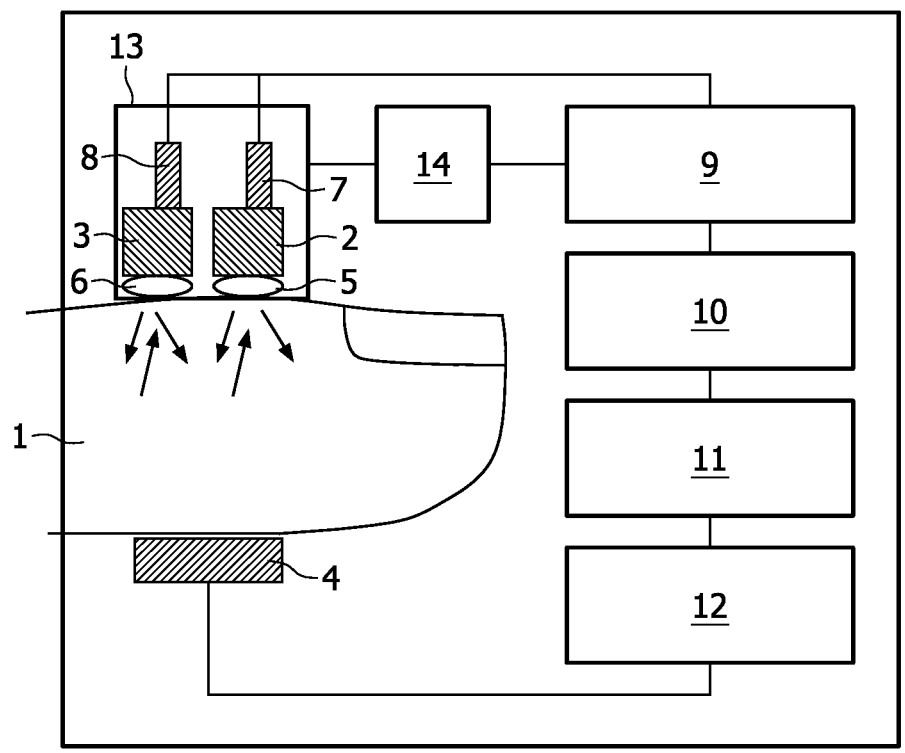
FIG. 4 is a schematic view of a blood oximeter according to a second preferred embodiment of the invention.

From FIG. 4 a blood oximeter according a second preferred embodiment of the invention can be seen. Further to the blood oximeter according to the first preferred embodiment of the invention, here, a force actuator 13 for pressing the lasers 2, 3 against the illuminated part of the fingertip 1, and a pressure controller 14 for applying a predefined pressure changing in time are provided. This provides for the possibility of simultaneously measuring the blood pressure as set out in the following.

The monitoring photodiodes 7, 8 measure the velocities of the red blood cells inside the fingertip 1. In order to see this information, measured data is split into intervals of 10 ms. The frequency spectrum of each of these intervals is calculated. A number of these spectra are shown in FIG. 5 with the relative time at which they were measured, all for the same force.

Figure 5:
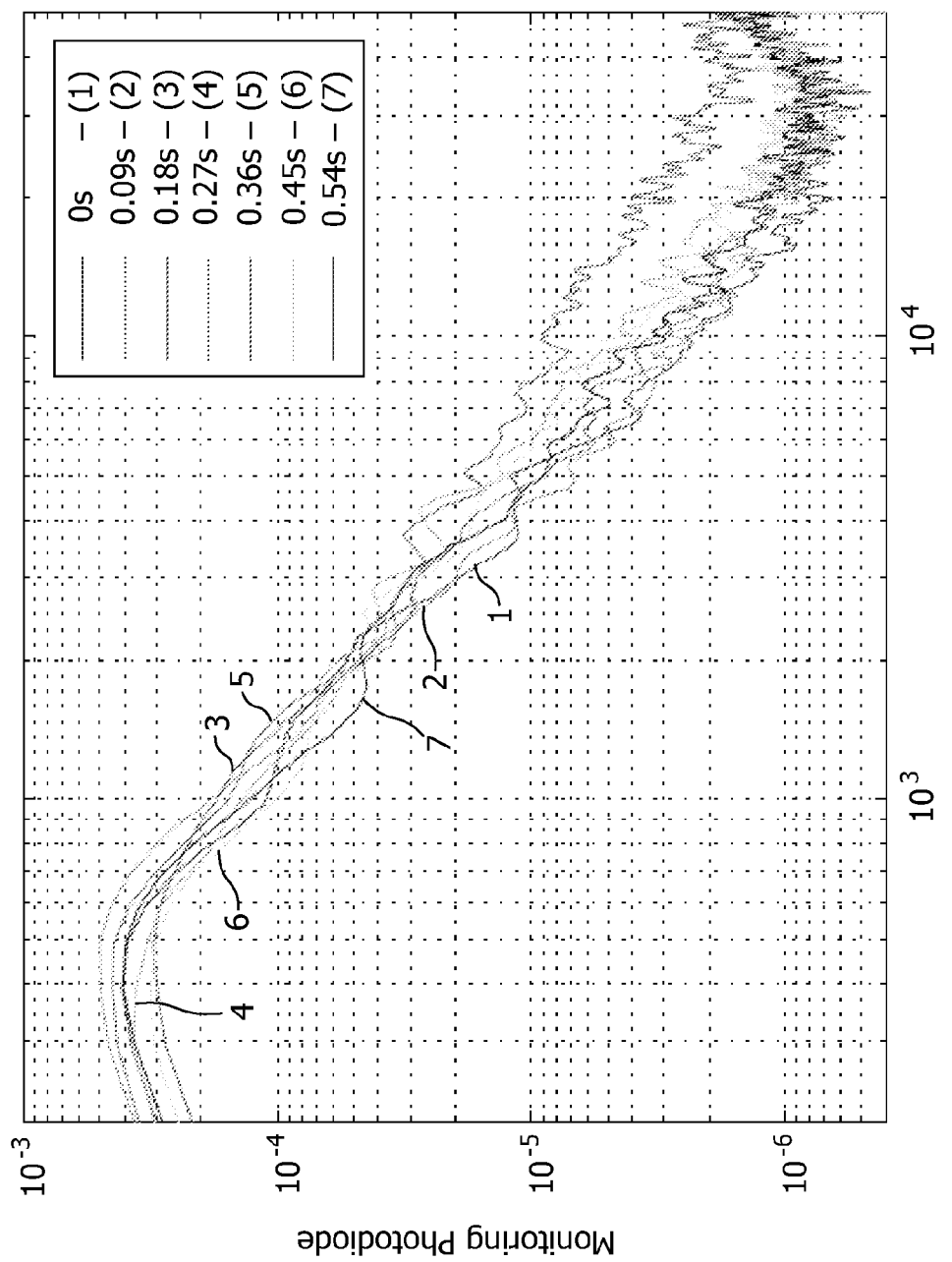
FIG. 5 shows the variation of the monitoring photodiode spectrum with the cardiac cycle.

FIG. 5 shows that the spectrum "dances" up and down between frequencies of about 10 kHz to 40 kHz. This is the effect of the cardiac cycle: The frequency of this variation of the spectrum is the heart rate. The measured velocities can be obtained using Doppler shift formula, and they correspond to the expected blood velocities at a depth corresponding to the focal lengths of the lenses 5, 6, which are 1.5 mm according to the preferred embodiments of the invention.

Figure 6A:
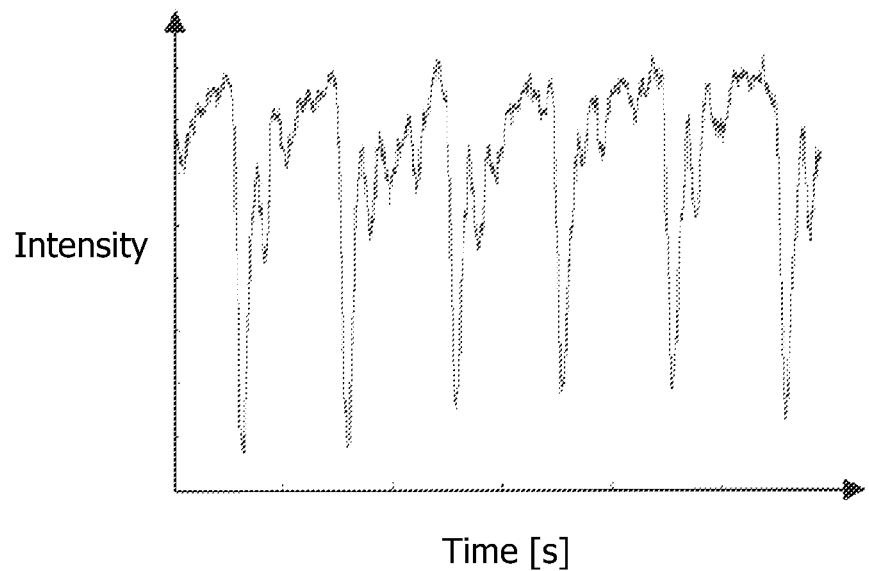
FIG. 6a shows the measured heart beat when a fingertip is pressed hard.
Figure 6B:
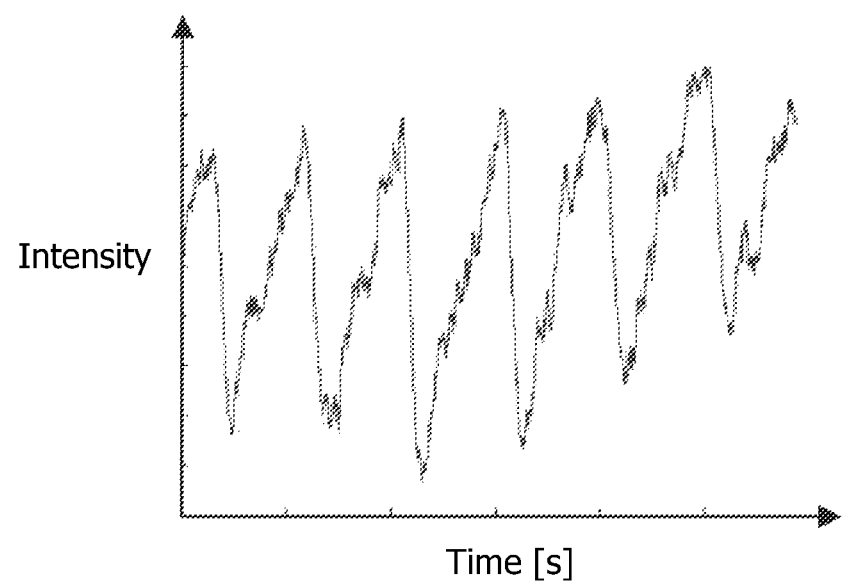
FIG. 6b shows the measured heart beat when the fingertip is pressed softly.

The signal can be plotted as a function of time if the spectrum is integrated in a certain frequency range and the energy is plotted in that spectrum as a function of time. The resulting signal shows the heart beat and is dependent on the force applied as can be seen from FIG. 6.

During the blood pressure measurements the force with which the force actuator 13 presses the lasers 2, 3 against the fingertip 1 is increased by the pressure controller 14, and for each value of the force a certain number of spectra are measured. When the applied pressure is lower than the diastolic pressure the blood flows during the entire cardiac cycle. When the pressure on the fingertip 1 is increased to a value higher than the diastolic pressure, the capillaries collapsed and blood stops flowing.

To measure the blood pressure, the dominant frequencies in the spectrum of one of the monitoring photodiodes 7, 8 can be determined. The "dancing" of the spectrum shows a frequency range of approximately 10 kHz to 40 kHz. When the force on the fingertip 1 is increased, the active part of the spectrum shifts to lower frequencies. This shift continues until the frequencies between 1 kHz and 2 kHz are the most active frequencies. This shift in active frequencies is also an indication of the diastolic and systolic transitions.

A method for evaluating the most active frequencies is the following:

1. For every cardiac cycle all spectra taken with monitoring photodiode 7 are calculated.
2. For every frequency, the maximum and the minimum of all these spectra are evaluated.
3. For every frequency, the ratio of this maximum and minimum is calculated.
4. The frequency at which this ratio is largest is the most active frequency.
5. This dominant frequency is evaluated for every cardiac cycle and plotted against the force applied by the force actuator 13.

Figure 7:
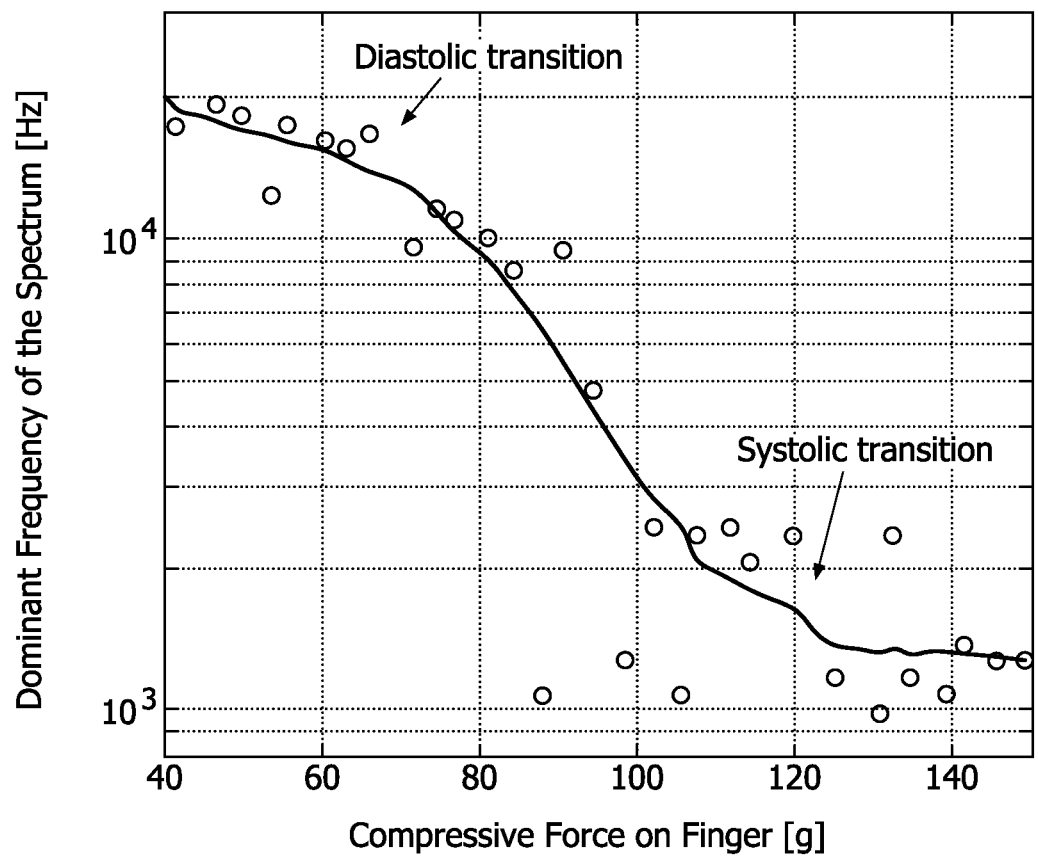
FIG. 7 shows diastolic and systolic transitions, respectively.

An example of the resulting plot with the transition from high dominant frequency to low dominant frequency is shown in FIG. 7. This transition was measured by slowly increasing the force on the fingertip 1 over a duration of one minute. As can be seen, the dominant frequency decreases when the force increases. The two transition points on the finger reflector systolic and diastolic transition, respectively.

As a result, compared with conventional blood oximeters, the invention allows for the following advantages:

The blood oximeter is more robust against environment light because it does not rely on the absolute intensity of the light as in conventional pulse oximetry.

The oxygen content in both veins and artery can be measured relying on different Doppler shift frequency bands and on the pulsating component.

Doppler shift oximetry provides an average concentration of oxygen in blood, i.e. both in veins and artery, at low perfusion. Even though a pulse may be hardly present in this case, the signal coming from the moving blood is present and the amount of light absorbed by the tissue is dependent on the oxygen concentration.

The blood oximeter according can be operated in a low power regime because it only needs a few tenths of a second of measurement and further can be operated in a pulsed mode. Accordingly, the device may have a quicker start, too.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. A blood oximeter for measuring the oxygenation and at least one other parameter of flowing blood in living tissue, comprising:
    an infrared light source configured to emit light of infrared wavelengths into the tissue;
    a red laser with a laser cavity configured to emit a red laser beam into the tissue, the red laser being adapted to allow a part of the red laser beam which is scattered by the tissue to re-enter into the laser cavity;
    a red laser beam sensor for measuring the light emitted from the red laser, the red laser beam sensor outputting a signal which varies in accordance with the self-mixing interferometric effect between the red laser beam and the scattered red laser beam;
    a pulse oximetry photodiode configured to receive the infrared wavelength light from the infrared light source which has passed through the tissues and to receive the red laser beam which has passed through the tissue from the red laser; and
    one or more processing units which receives and processes output signals from the red laser beam sensor and the pulse oximetry photodiode to determine an arterial blood oxygen concentration and the at least one other parameter.

2. The blood oximeter according to claim 1, wherein the one or more processing units further process the received signals to determine a venous blood oxygen concentration.

3. The blood oximeter according to claim 1, further including:
    a lens disposed between the red laser and the tissue, the lens being configured to directly contact the illuminated tissue.

4. The blood oximeter according to claim 1, further including:
   a pulse controller which pulses the red laser in pulses of 20ms or less and switches the red laser off between pulses to conserve energy.

5. The blood oximeter according to claim 1, further including:
   a force actuator adapted to apply a force to the tissue; and
   a force controller which controls the force actuator to apply a time varying force to the tissue; and
   wherein the one or more processing units further determines blood pressure from the applied force and the received signals.

6. The blood oximeter according to claim 5, wherein the infrared light source is a laser and further including:
   an infrared laser beam sensor for measuring the light emitted from the infrared sensor and outputs a signal to the one or more processing units.

7. The blood oximeter according to claim 1, wherein the one or more processing units further determine both blood flow velocity and relative movement between the tissue and the red laser from the signals received from the laser beam sensor and the pulse oximetry photodiode.

8. A blood oximeter for measuring the oxygenation and blood pressure of flowing blood in living tissue, comprising:
   two light sources emitting light of different wavelengths into the tissue, at least one of the light sources being a laser with a laser cavity emitting a laser beam, the laser being configured to allow a part of the laser beam which is scattered by the tissue to re-enter into the laser cavity;
   a laser beam sensor which measures the light emitted from the laser to obtain a signal which varies in accordance with a self-mixing interferometric effect between the original laser beam and the scattered laser beam;
   a force actuator adapted to press the light sources against the illuminated tissue with a pressure;
   a force controller that varies the pressure in time over a range at least between a pressure which permits blood flow through the tissue and a pressure which blocks the blood flow; and
   one or more processing units which determines the blood pressure from the signal from the laser beam sensor and the pressure applied by the force actuator.

9. The blood oximeter according to claim 8, wherein the one or more processing units determines dominant frequencies in a spectrum of the signal from the laser beam sensor and plots at least one dominant frequency against the applied pressure to determine diastolic and systolic transitions.

10. The blood oximeter according to claim 8, wherein the one or more processing units further determine pulse rate, blood oxygen, and blood velocity.

11. The blood oximeter according to claim 8, wherein the first and second light sources are both lasers whose emitted light is measured by a pair of laser beam sensors and further including:
   a SO2 unit for determining and indicating an SO2 value based on the signals of both of the laser beam sensors.

12. A blood oximeter comprising:
   an infrared laser which emits infrared laser light;
   an infrared beam sensor which measures the light emitted by the infrared laser using self-mixing interferometry;
   a first lens configured to be pressed against tissue, the first lens being optically coupled to the infrared laser to focus the infrared laser light into the tissue;
   an red laser which emits red laser light;
   an red beam sensor which measures the light emitted by the red laser using self-mixing interferometry;
   a second lens configured to be pressed against the tissue, the second lens being optically coupled to the red laser to focus the red laser light into the tissue;
   one or more processing units configured to:
      determine red and infrared Doppler shift spectra from the emitted light measured by the red and infrared beam sensors, the Doppler shift spectra having a pulsing part indicative of blood moving in the arteries and a non-pulsing part indicative of blood in the veins;
      determining blood oxygen concentration by comparing the red and infrared spectra.

13. The blood oximeter according to claim 12, wherein the one or more processors determine both arterial blood oxygen concentration and venous blood oxygen concentration.

14. The blood oximeter according to claim 13, wherein the one or more processing units is further configured to determine the venous blood oxygen concentration in tissue with low perfusion by:
   determining energies of the red and infrared spectra;
   normalizing the energy of the red spectrum by dividing the enery of the red spectrum by the energy of the infrared spectrum;
   integrating over the normalized red spectrum.

15. The blood oximeter according to claim 14, wherein the red and infrared beam sensors measure reflected light and further including:
   a photodiode which measures red and infrared light which has passed through the tissue and sends signals to the one or more processing units indicative thereof.

16. The blood oximeter according to claim 12, further including:
   a force actuator which presses at least the first and second lenses against the tissue;
   a force controller that varies the pressure in time at least between a pressure which permits blood flow through the tissue and a pressure blocks blood flow; and
   wherein the one or more processing units is further programmed to determine blood pressure from the signals from the red and infrared beam sensors and the pressure applied by the force actuator.

* * * * *